United States Patent [19]
Wong et al.

[11] Patent Number: 5,082,866
[45] Date of Patent: Jan. 21, 1992

[54] BIODEGRADABLE ABSORPTION ENHANCERS

[75] Inventors: Ooi Wong, Lawrence, Kans.; Toshiaki Nishiahta, Ibaraki, Japan; Joseph H. Rytting, Lawrence, Kans.

[73] Assignee: Odontex, Inc., Lawrence, Kans.

[21] Appl. No.: 566,758

[22] Filed: Aug. 14, 1990

Related U.S. Application Data

[62] Division of Ser. No. 201,029, Jun. 1, 1989, Pat. No. 4,980,378.

[51] Int. Cl.$^5$ ............................................. A61K 47/00
[52] U.S. Cl. ............................ 514/785; 514/420; 514/946; 514/947
[58] Field of Search ................ 514/947, 785, 946, 420

[56] References Cited

U.S. PATENT DOCUMENTS

| | | | |
|---|---|---|---|
| 2,135,641 | 11/1938 | Jacobson | 560/155 |
| 2,290,174 | 7/1942 | Epstein | 560/155 |
| 2,293,026 | 8/1942 | Day | 560/155 |
| 2,293,034 | 8/1942 | Moore | 560/155 |
| 3,899,585 | 8/1975 | Misato | 514/551 |
| 4,032,325 | 6/1977 | Kida | 71/95 |
| 4,732,892 | 3/1988 | Sarpotdar | 514/947 |
| 4,822,773 | 4/1989 | Alexander | 514/947 |

FOREIGN PATENT DOCUMENTS 57-88113 6/1982 Japan .
58-57309 4/1983 Japan .

*Primary Examiner*—Michael L. Shippen
*Attorney, Agent, or Firm*—Zarley, McKee, Thomte, Voorhees & Sease

[57] ABSTRACT

Biodegradable absorption enhancers, especially useful in pharmaceutical formulations, are compounds having the formula

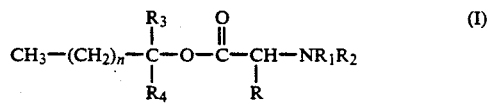

(I)

wherein R is hydrogen, $C_1$-$C_7$ alkyl, benzyl or 4-hydroxybenzyl; n is a whole number from 4 to 18 inclusive; $R_1$ and $R_2$ are independently selected from hydrogen and $C_1$-$C_7$ alkyl, or $R_1$ and $R_2$ together with the nitrogen atom to which they are attached are combined to form a substituted or unsubstituted heterocycloalkyl radical having a total of 5 to 7 ring atoms, optionally including a hetero ring atom selected from oxygen, sulfur and nitrogen in addition to the indicated nitrogen atom, the substituents when present being one to three $C_1$-$C_7$ alkyl radicals, which may be the same or different; and $R_3$ and $R_4$ are independently selected from hydrogen, methyl and ethyl.

7 Claims, 2 Drawing Sheets

BIODEGRADABLE ABSORPTION ENHANCERS

This is a divisional of copending application Ser. No. 201,029, filed on June 1, 1989, now U.S. Pat. No. 4,980,378.

FIELD OF THE INVENTION

The invention relates to the development of safe and effective agents which improve the rate of percutaneous and oral mucosal transport of physiologically active agents. More particularly, the present invention relates to an improved topical penetration enhancer for use in the topical delivery of a local or systemic physiologically active agent to a mammalian organism.

BACKGROUND ART

Dermal drug formulations may represent the oldest drug dosage form in human history. It is highly probable that even ancient people used resins and animal fats to treat damage to the skin resulting from injuries and burns. The use of such dermal formulations for local effect remained largely unchanged until the middle of this century. The concept of administering drugs through the skin to achieve a local or systemic effect was first seriously advocated by Dr. Alejandro Zaffaroni in the early 1970's. Since that time extensive research has been undertaken in this field.

The transdermal route of drug administration offers a number of advantages over the more conventional routes of drug administration. For instance, a drug may be delivered to targeted tissues from adjacent skin areas. The transdermal route of drug administration also allows for a gradual, controlled release of drug into the systemic circulation. Since many drugs are poorly absorbed or delivered through the traditional routes of administration, the transdermal route provides an effective method of achieving improved bioavailability for those drugs. The transdermal route of drug administration is also advantageous since the administration of dermally administered drugs may be easily stopped should an undesirable side effect occur during therapy.

In spite of the foregoing advantages, transdermal formulations are limited. They cannot be used with most polar drugs since they tend to penetrate the skin too slowly. This characteristic is particularly crucial since most drugs are of a polar character. In addition, many drugs elicit a reaction and/or irritation at the site of topical application.

Two methods are known for improving the rate of penetration of polar drugs across the skin. The first method is to make a better formulation of the drug to increase its thermodynamic activity. The thermodynamic activity of a drug in a dermal formulation is dependent on the concentration of the drug and the choice of the vehicle. According to the laws of thermodynamics, the maximum activity of the drug is usually fixed by that of the pure state, i.e., the drug crystal. The second method involves the use of compounds or penetration enhancers to increase the permeability of the barrier membrane. The latter method is generally more practical because of its convenience and effectiveness.

Thus, in the last two decades, a wide variety of compounds have been evaluated as to their effectiveness in enhancing the rate of penetration of drugs through the skin. The classically recognized strong enhancers tend to be proton accepting solvents, e.g., dimethyl sulfoxide (DMSO) and dimethyl acetamide (DMA). Recently, 2-pyrrolidone, N,N-diethyl-m-toluamide (Deet), 1-dodecylazacycloheptane-2-one (Azone, a registered trademark of Nelson Research), N,N-dimethylformamide, N-methyl-2-pyrrolidone and calcium thioglycolate have been reported as effective enhancers. The structures of these compounds are set forth in Table I.

TABLE I

| Compound | Structure |
|---|---|
| Dimethyl Sulfoxide (DMSO) | $(CH_3)_2S=O$ |
| N,N-Dimethyl Acetamide (DMA) | $(CH_3)_2N-C(=O)-CH_3$ |
| N,N-Diethyl-m-Toluamide (Deet) | m-$CH_3$-$C_6H_4$-$CON(C_2H_5)_2$ |
| 1-Dodecylazacycloheptane-2-One (Azone or laurocapram) | azepan-2-one with $N(CH_2)_{11}CH_3$ |
| 2-Pyrrolidone-5-Carboxylic Acid | HOOC-substituted pyrrolidin-2-one (N-H) |
| 2-Pyrrolidone | pyrrolidin-2-one (N-H) |
| N,N-Dimethylformamide | $(CH_3)_2N-C(=O)-H$ |
| N-methyl-2-pyrrolidone | 1-methylpyrrolidin-2-one |
| calcium thioglycolate | $CaCH_2COOS \cdot 3H_2O$ |

See, for example, the review article by Kenneth A. Walters entitled "Percutaneous absorption and transdermal therapy," *Pharmaceutical Technology*, March 1986, pp. 30–46, which discusses the use of surfactants and penetration enhancers to improve skin transport and their possible mechanisms of action.

Several problems have been associated with these prior art dermal enhancers. They cannot be applied to most polar drugs because they tend to penetrate the skin too slowly. And many of these prior art dermal enhancers produce reactions and/or irritation at the site of application.

In the search for new dermal penetration enhancers, Rinta Iubuki, in his Ph.D. Thesis in 1985 at the University of Kansas entitled "Use of Snake Skin as a Model Membrane for Percutaneous Absorption Studies," investigated the use of six compounds for transdermal penetration enhancement of indomethacin in a dosage form of a petrolatum ointment. The compounds disclosed in his thesis are presented below:

The primary problem with these compounds is their toxicity. Obviously, if a compound when used as a dermal enhancer is either toxic, irritating or allergic, then that compound is unsuitable for application to the human body. DMSO and DMA are also not clinically acceptable for those reasons. Deet and Azone have lower reported toxicities yet their toxicity is high enough such that they are not widely used.

In developing effective dermal enhancers, it would be advantageous to evaluate the potential enhancers by in vivo determination of the rate of human skin penetration of a drug administered along with the enhancer. The amount of drug could be measured in the host's circulation or in the target tissue. Unfortunately, due to the risks involved and the cost of such an evaluation, human in vivo determination is not practical. Thus, researchers have used a variety of mammals for in vivo study. Typical mammals include mice, rats, rabbits, pigs and dogs. However, significant differences have been found in the pattern of drug penetration among these mammals and humans. Although the reason for this species variation has not been well-established, the difference in the density of hair follicles is considered to be a factor.

Thus, the disadvantage of in vivo methods has encouraged wide use of various in vitro methods. Copending application U.S. Ser. No. 901,732, filed Aug. 29, 1986, incorporated by reference herein, discloses a novel method for in vitro determination of transdermal absorption. The method involves the use of shed snake skin.

In spite of the numerous attempts in the art to prepare a method for enhancing the absorption of drugs, especially polar drugs, through the skin, there still exists a clear and present need in the art for a method to enhance the absorption of drugs through the skin. This need has been addressed by co-pending application U.S. Ser. No. 096,092, filed Sept. 11, 1987, which describes a novel group of cyclic urea compounds which enhance the absorption of active substances through the skin while avoiding the significant pharmacological activities and toxicities of the prior art enhancers. The soft penetration enhancers of Ser. No. 096,092 have the formula wherein R, $R_1$ and $R_2$ are independently selected from hydrogen; hydroxy; fluorine; bromine; chlorine; $C_1$-$C_{20}$ alkyl; $C_2$-$C_{20}$ alkenyl; $C_2$-$C_{20}$ alkynyl; $C_3$-$C_{10}$ cycloalkyl; $C_2$-$C_{20}$ (monohydroxy or polyhydroxy)alkyl; $C_1$-$C_{20}$ (monohalo or polyhalo)alkyl; carboxy; $C_1$-$C_{20}$ alkylcarboxy; $C_1$-$C_{20}$ alkenylcarboxy; $C_1$-$C_{20}$ carboxyalkyl; $C_1$-$C_{20}$ alkanoyl; $C_1$-$C_{20}$ alkanoyloxy; $C_1$-$C_{20}$ alkoxycarbonyl; carbamoyl; carbamyl; $C_1$-$C_{20}$ alkylcarbamyl; sulfo; $C_1$-$C_{20}$ alkylsulfonyl; $C_1$-$C_{20}$ alkylsulfinyl; $C_1$-$C_{20}$ alkylsulfoxide; $C_1$-$C_{20}$ alkylsulfone; thio; $C_1$-$C_{20}$ alkylthio; amino; nitro; $C_1$-$C_{20}$ alkylamino; $C_1$-$C_{20}$ aminoalkyl; substituted or unsubstituted phenyl or benzyl, the substituents being selected from hydroxy, fluorine, bromine, chlorine, $C_1$-$C_{20}$ alkyl, $C_2$-$C_{20}$ alkenyl, $C_2$-$C_{20}$ (monohydroxy or polyhydroxy)alkyl; X is methylene or oxygen and n is 0 to 20.

Improvement of transdermal drug delivery has thus been a focus of pharmaceutical research for many years. However, the stratum corneum presents a formidable barrier to percutaneous drug absorption. This barrier function is believed to be due to the ordered matrix of intercellular lipids and to the low water content in the stratum corneum. Since human gingivae also have stratum corneum, the problems besetting development of gingival formulations are much the same. There is clearly a need for additional novel compounds which enhance the absorption of active substances through the skin and mucous membranes such as the gingivae, but which are designed to have greatly reduced toxicity.

SUMMARY OF THE INVENTION

Surprisingly, the present inventors now find that a novel group of long chain alkyl (N,N-disubstituted amino)acetates and related compounds enhance the absorption of active substances through the skin and mucous membranes while avoiding the significant pharmacological activities and toxicities of the classical prior art enhancers. The present invention thus provides a new class of biodegradable soft penetration enhancers which because of their structure have less adverse or toxic effects but which are nevertheless excellent promoters of percutaneous and oral mucosal (especially gingival) absorption.

The soft penetration enhancers of the present invention have the structural formula wherein R is hydrogen, $C_1$-$C_7$ alkyl, benzyl or 4-hydroxybenzyl; n is a whole number from 4 to 18 inclusive; $R_1$ and $R_2$ are independently selected from hydrogen and $C_1$-$C_7$ alkyl, or $R_1$ and $R_2$ together with the nitrogen atom to which they are attached are combined to form a substituted or unsubstituted heterocycloalkyl radical having a total of 5 to 7 ring atoms, optionally including a hetero ring atom selected from oxygen, sulfur and nitrogen in addition to the indicated nitrogen atom, the substituents when present being one to three $C_1$-$C_7$ alkyl radicals, which may be the same or different; and $R_3$ and $R_4$ are independently selected from hydrogen, methyl and ethyl.

The present invention also provides a method for carrying physiologically active agents through body surfaces such as skin and mucous membranes and to compositions for use in that method. More specifically, the invention relates to a method for increasing the penetration of a physiologically active agent across the skin or mucous membrane of a mammalian organism comprising topically applying a physiologically active agent in an amount sufficient to achieve the desired local or systemic effect and the soft penetration enhancing compound described above in an amount sufficient to effectively increase penetration of the physiologically active agent. The invention further provides a pharmaceutical composition comprising same along with a pharmaceutically acceptable carrier therefor.

DETAILED DESCRIPTION OF THE INVENTION AND THE PREFERRED EMBODIMENTS

The long chain alkyl (N,N-disubstituted amino)acetates of the present invention may be described as "soft" dermal penetration enhancers since subsequent to exerting their desired effect, they "cleave" via chemical and/or enzymatic hydrolysis to release nontoxic byproducts. Without being bound by any particular theory, it is believed that an active ingredient and a soft penetration enhancer are released from a topical formulation and the soft enhancer would then exert its penetration enhancing effect. The soft or biodegradable penetration enhancer, either during or after penetration, would be broken down by skin enzymes, e.g. esterases, into a long chain alkanol and a substituted amino acid. In this way, the toxicity of the soft penetration enhancer would be greatly reduced. The possible cleavage of the soft penetration enhancer is set forth below:

Subcutaneous tissues also contain esterases, so the esters break down during and after incorporation, but before reaching the systemic circulation. The penetration enhancers of the invention may act like biodegradable surfactants in that, after they exert their penetration enhancing effects on drug transport from the topical dosage form, they will be fragmented into smaller compounds, thus reducing toxicity.

The alkanols and amino acids to which the present enhancers are initially converted by esterases may themselves act as strong enhancers. Alkanols are widely used moisturizers in the cosmetic field and are known to increase transport across the stratum corneum. However, they are weak in practical use, due to their slow incorporation into the stratum corneum. On the other hand, compounds with amino groups are rapidly incorporated into skin.

As noted earlier, the prior art absorption enhancers have significant pharmacological activities and toxicities. The compounds of the present invention, on the other hand, are a new class of enhancers which, because of their structure, do not demonstrate a significant adverse effect on the skin or mucous membranes and yet are excellent promoters of percutaneous absorption. The toxicity of known enhancers is generally due to the fact that they are not metabolized by pathways which would diminish their toxicity. To minimize toxicity, the basic structure of the synthesized enhancer should be selected to resemble those biological substances which are well-known metabolites. The enhancers of the present invention were specifically designed to be metabolized in a non-toxic fashion. Moreover, the present compounds are liquid so they can be readily incorporated into the skin.

The long chain alkyl (N,N-disubstituted amino)acetates and related compounds of the present invention have the formula:

wherein R is hydrogen; $C_1$-$C_7$ alkyl, benzyl or 4-hydroxybenzyl; n is a whole number from 4 to 19 inclusive, and $R_1$ and $R_2$ are independently selected from hydrogen and $C_1$-$C_7$ alkyl, or $R_1$ and $R_2$ together with the nitrogen atom to which they are attached are combined to form a substituted or unsubstituted heterocycloalkyl radical having a total of 5 to 7 ring atoms, optionally including a hetero ring atom selected from oxygen, sulfur and nitrogen in addition to the indicated nitrogen atom, the substituents when present being one to three $C_1$-$C_7$ alkyl radicals, which may be the same or different; and $R_3$ and $R_4$ are independently selected from hydrogen, methyl and ethyl.

The alkyl radicals may be straight or branched, i.e. methyl, ethyl, propyl, butyl, pentyl, hexyl and heptyl, and the branched chain groups isomeric therewith.

When $R_1$ and $R_2$ are combined with the adjacent nitrogen atom such that represents a heterocycloalkyl radical, illustrative such heterocycloalkyl radicals include morpholino, 1-pyrrolidinyl, perhydro-1,2,4-oxathiazin-4-yl, 1- or 4-piperazinyl, 4-methyl-1-piperazinyl, piperidino, hexamethyleneimino, 2-methyl-1-pyrazolidinyl, 1- or 2-pyrazolidinyl, 3-methyl-1-imidazolidinyl and 1- or 3-imidazolidinyl.

In preferred embodiments of the invention, the substituents in formula (I) have one or more of the following values:

(1) R is hydrogen;
(2) n is 6, 8, 10 or 12; and
(3) $R_1$ and $R_2$ are both methyl or both ethyl, or together with the adjacent nitrogen atom represent a 4-methyl-1-piperazinyl radical, i.e. a radical of the formula and
(4) $R_3$ and $R_4$ are both hydrogen.

Particularly preferred compounds of the present invention include dodecyl (N,N-dimethylamino)acetate, decyl (N,N-dimethylamino)acetate and octyl (N,N-dimethylamino)acetate.

The compounds of formula (I) are readily prepared via a two-step synthesis. In the first step, long chain alkyl chloroacetates are prepared by reaction of the corresponding long chain alkanols with chloromethyl chloroformate or the like in the presence of an appropriate base such as triethylamine, typically in a suitable solvent such as chloroform. The reaction can be depicted as follows:

wherein R, $R_3$, $R_4$ and n are as defined as above. The reaction temperature may be selected from about 10° C. to about 200° C. or reflux; however, room temperature is preferred. The use of a solvent is optional. If a solvent is used, a wide variety of organic solvents may be selected. Choice of a base likewise is not critical. Preferred bases include tertiary amines such as triethylamine, pyridine and the like. Reaction time generally extends from about one hour to three days.

In the second step, the long chain alkyl chloroacetate is condensed with an appropriate amine according to the scheme:

wherein n, R, $R_1$, $R_2$, $R_3$ and $R_4$ are defined as before. Excess amine reactant is typically used as the base and the reaction is conveniently conducted in a suitable solvent such as ether. The reaction is preferably run at room temperature; however, other temperatures may be selected above or below room temperature, as in the first synthetic step. Again, reaction time usually varies from about one hour to several days.

The amount of the penetration enhancer of formula (I) which may be used in the present invention is an effective, non-toxic amount for enhancing absorption either through the skin or mucous membranes. Generally, this amount ranges from about 1 to about 95 weight percent of the topical composition. Preferably, about 0.5 to about 40 weight percent of the penetration enhancer is used in the composition.

The compounds described herein are useful in improving percutaneous or mucous membrane absorption of physiologically active agents. The term "percutaneous" means transdermal or transcutaneous; it denotes the passage of substances through unbroken skin. While the term "mucous membrane absorption" refers generally to any of the mucous membranes in the body, absorption through the mucous membranes of the oral cavity is of particular interest. Thus, buccal, sublingual, gingival and palatal absorption are specifically contemplated by the present invention. In a preferred embodiment, the instant penetration enhancers are used to improve absorption through those oral tissues which most resemble the skin in their cellular structure, i.e. the gingivae and palate. The term "physiologically active agent" is used herein to refer to a broad class of useful chemical and therapeutic agents including physiologically active steroids, antibiotics, antifungal agents, antibacterial agents, antineoplastic agents, analgesics and analgesic combinations, anorexics, anthelmintics, antiarthritics, antiasthma agents, anticonvulsants, antidepressants, antidiabetic agents, antidiarrheals, antihistamines, anti-inflammatory agents, antimigraine preparations, antimotion sickness preparations, antinauseants, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, betablockers, antiarrhythmics, antihypertensives, diuretics, vasodilators including general, coronary, peripheral and cerebral; central nervous system stimulants, cough and cold preparations, decongestants, hormones, hypnotics, immunosuppressives, muscle relaxants, parasympatholytics, parasympathomimetics, psychostimulants, sedatives, tranquilizers, allergens, antihistaminic agents, anti-inflammatory agents, physiologically active peptides and proteins, ultraviolet screening agents, perfumes, insect repellents, hair dyes, and the like. The term "physiologically active" in describing the agents contemplated herein is used in a broad sense to comprehend not only agents having a direct pharmacological effect on the host but also those having an indirect or observable effect which is useful in the medical arts, e.g. the coloring or opacifying of tissue for diagnostic purposes, the screening of U.V. radiation from the tissues and the like.

For instance, typical fungistatic and fungicidal agents include thiabendazole, chloroxine, amphotericin, candicidin, fungimycin, nystatin, chlordantoin, clotrimazole, ethonam nitrate, miconazole nitrate, pyrrolnitrin, salicylic acid, fezatione, ticlatone, tolnaftate, triacetin, zinc, pyrithione and sodium pyrithione.

Steroids include cortisone, cortodoxone, fluoracetonide, fludrocortisone, difluorsone diacetate, flurandrenolone acetonide, medrysone, amcinafel, amcinafide, betamethasone and its esters, chloroprednisone, clorcortelone, descinolone, desonide, dexamethasone, dichlorisone, difluprednate, flucloronide, flumethasone, flunisolide, fluocinonide, flucortolone, fluoromethalone, fluperolone, fluprednisolone, meprednisone, methylmeprednisolone, paramethasone, prednisolone and prednisone.

Antibacterial agents include sulfonamides, penicillins, cephalosporins, penicillinase, erythromycins, lincomycins, vancomycins, tetracyclines, chloramphenicols, streptomycins, and the like. Specific examples of antibacterials include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxytetracycline, minocycline, and the like.

Peptides and proteins include, in particular, small to medium-sized peptides, e.g., insulin, vasopressin, oxytocin and human growth hormone.

Other agents include iododeoxyuridine, podophylline, theophylline, isoproterenol, triamicinolone acetonide, hydrocortisone, indomethacin, phenylbutazone paraaminobenzoic acid, aminoprionitrile and penicillamine.

The foregoing list is by no means intended to be exhaustive and any physiologically active agent may be applied by the method of the present invention.

An important advantage of the present invention is that absorption of polar bioactive agents as well as nonpolar drugs is also improved. The polar bioactive agents encompass a variety of therapeutic agents such as the xanthines, triamterene and theophylline, the antitumor agents, 5-fluorouridinedeoxyriboside, 6-mercaptopurinedeoxyriboside, vidarabine, the narcotic analgesics, hydromorphone, cyclazine, pentazocine, bupomorphine, the compounds containing organic anions, heparin, prostaglandins and prostaglandin-like compounds, cromolyn sodium, carbenoxolone, the polyhydroxylic compounds, dopamine, dobutamine, 1-dopa, $\alpha$-methyldopa, the polypeptides, angiotensin antagonists, bradykinin, insulin, ACTH, enkaphaline, endorphin, somatostatin, secretin and miscellaneous compounds such as tetracyclines, tromocriptine, lidocaine, cimetidine or any related compounds. The quantity of these polar bioactive agents necessary for preparing the drug form could vary over a wide range, but would normally be regulated by that quantity necessary to comprise the therapeutically effective dosage form.

Agents normally applied as eye drops, ear drops or nose drops or into the membranes of the oral cavity are also more effective when applied along with the penetration enhancers of the present invention.

As indicated earlier, agents used in diagnosis may be used more effectively when applied dissolved in one of the vehicles of this invention. Patch tests to diagnose allergies may be effected promptly without scratching the skin or covering the area subjected to an allergen when the allergens are applied along with the enhancers of this invention.

This invention is also useful in topical application of cosmetic or esthetic agents. For example, compounds such as melanin-stimulating hormone (MSH) or dihydroxy acetone and the like are more effectively applied to skin to simulate a suntan when they are applied along with the enhancers of this invention. The agent is carried into the skin more quickly and in greater quantity when applied in accordance with this invention. Hair dyes also penetrate more completely and effectively when dissolved in one of the vehicles of this invention.

While the foregoing discussion describes the simultaneous administration of the physiologically active agent along with the penetration enhancer, the penetration enhancer may be applied before or after to the application of the physiologically active agent, if desired.

The physiologically active agents intended for use in the practice of the present invention are intended for either their systemic effect or for their local effect.

Dosage forms for topical application to the skin or mucous membranes of humans and animals include creams, lotions, gels, ointments, suppositories, sprays, for example nasal sprays, aerosols, buccal and sub-lingual tablets, gingival and buccal patches or any one of a variety of transdermal devices for use in the continuous administration of systemically active drugs by absorption through the skin, oral mucosa or other membranes, see for example, one or more of U.S. Pat. Nos. 3,598,122, 3,598,123, 3,731,683, 3,742,951, 3,814,097, 3,921,636, 3,971,995, 3,993,072, 3,993,073, 3,996,934, 4,031,894, 4,060,084, 4,069,307, 4,201,211, 4,230,105, 4,292,299 and 4,292,303 and U.S. Pat, No. 4,077,407. The foregoing patents also disclose a variety of specific systemically active agents which may also be useful in transdermal delivery, which disclosures are hereby incorporated herein by reference.

The usual pharmaceutical compounding agents, diluents or carriers may be included in these compositions as desirable for the particular route of administration and dosage form. The amount and type of diluent or carrier used should, of course, be consistent with the compatibility of the agent with the compound of this invention. For instance, a cosolvent or other standard adjuvant, such as a surfactant, may be necessary to maintain the agent in solution or suspension at the desired concentration.

For nasal sprays and other mucous membrane applications isotonic saline may be preferable as a diluent. The instant enhancer may be present in these forms in various concentrations, for example, from about 2% to about 75% by weight or higher.

Lotions and gels, ointments or creams, may contain the usual ingredients to provide a base, as for example cetyl alcohol, an emulsifier such as lauryl sulfate and water. Another base may be formulated by combining equal weight amounts of stearic acid, cetyl alcohol, triethanolamine and glycerol monostearate with water. Still other bases may utilize polyethylene glycols of different viscosities, depending upon the desired consistency.

A suppository form may be made from a high viscosity polyethylene glycol 4000, water and the penetration enhancer.

Typical inert carriers which may be included in the foregoing dosage forms include conventional formulating materials, such as, for example, water, acetone, isopropyl alcohol, freons, ethyl alcohol, polyvinyl pyrrolidone, propylene glycol, fragrances, gel-producing materials such as "Carbopol", mineral oil, stearyl alcohol, stearic acid, spermaceti, sorbitan monooleate, "Polysorbates", "Tweens", sorbital, methylcellulose, and the like. The compositions of the present invention are formulated with any suitable nontoxic pharmaceutically acceptable inert carrier material. Such carrier materials are well known to those skilled in the art of pharmaceutical formulations. For those not skill in the art, reference is made to the text entitled, "REMINGTON'S PHARMACEUTICAL SCIENCES," 17th edition, 1985, ed. Alfonso R. Gennaro, Mack Publishing Company, Easton, Pa. 18042.

Any type of transdermal drug delivery system is also suitable in the practice of the present invention, for instance, the transdermal patch. A variety of transdermal drug delivery systems are disclosed and described in U.S. Pat. No. 4,624,665, herein incorporated by reference.

The amount of the composition, and thus of the physiologically active agent therein, to be administered will obviously be an effective amount for the desired result expected therefrom. This, of course, will be ascertained by the ordinary skill of the practitioner. Due to enhanced activity which is achieved, the dosage of the physiologically active agent may often be decreased from that generally applicable. In accordance with the usual prudent formulating practices, a dosage near the lower end of the useful range of the particular agent may be employed initially and the dosage increased as indicated from the observed response, as in the routine procedure of the physician.

The concentration of physiologically active agent in the various dosage forms is, of course, commensurate with that normally utilized for the particular agent in conventional formulations for effective results for the intended route. Both the amount of physiologically active agent and the amount of penetration enhancer will be influenced by the type of effect desired. To a certain degree, if a more localized effect is required, as for example, in treating a superficial infection with an antibacterial agent, lower amounts of physiologically active agents and lower concentrations of enhancer may be called for. Where deeper penetration is desired, as in the case of local anaesthesia, a higher concentration of enhancer may be desirable to promote adequate penetration. Where general systemic concentration of an agent is desired for a topical preparation, generally higher concentrations of enhancer are desirable and the amount of agent as, for example, a steroid, may be included in the composition sufficient to provide the blood level desired.

In order to further illustrate the present invention and the advantages thereof, the following specific examples are given, it being understood that same are intended only as illustrative and in nowise limitative.

EXAMPLE 1

Preparation of Dodecyl Chloroacetate

A mixture of dodecanol (10 g, 0.054 mol), chloromethyl chloroformate (6 g, 0.05 mol) and triethylamine (5.5 g) in 40 ml of dry chloroform was stirred at room temperature for 16 hours. The reaction mixture was then washed twice with water (50 ml per washing) and the organic phase was dried over anhydrous magnesium sulfate. Removal of the solvent gave 13 3 g (94% yield) of liquid product, which was chromatographed through a column of Florisil using chloroform as the eluent. $^1$HNMR(CCl$_4$) $\delta$0.90(3H, t, CH$_3$); 1.28[20 H, s, broad, —(CH$_2$)$_{10}$—]; 3.93(2H, s, —CH$_2$Cl); 4.11(2H, t, J=6Hz, —CH$_2$—O). $\nu_{max}$ (film): 2940, 2880(CH); 1765, 1745(C=O); 1180 (—C—O—C—)cm$^{-1}$.

EXAMPLE 2

Preparation of Dodecyl (N,N-dimethylamino)acetate

Dodecyl chloroacetate (5.5 g, 0.021 mol) was dissolved in 20 ml of ether and the resultant solution was cooled in an ice-bath. Dimethylamine (40 ml, 0.1M in ether) was added to the cooled solution of dodecyl chloroacetate. The reaction mixture was stirred at room temperature for two hours, then filtered through a filter paper to remove the white solid which formed. The filtrate was concentrated to give a liquid product which was chromatographed through a column of silica gel (60–200 mesh) using ethyl acetate as the eluent. The purity of the fractions was checked by thin layer chromatography. The pure fractions were combined and the solvent was removed by a rotary evaporator under reduced pressure to afford 5.8 g (100% yield) of dodecyl (N,N-dimethylamino)acetate. $^1$HNMR(CCl$_4$) $\delta$0.83(3H, t, CH$_3$); 1.20[20 H, s, broad, —(CH$_2$)$_{10}$]; 2.23[6H, s, (CH$_3$)$_2$N—]; 3.0 (2H, s, —CH$_2$—N); 3.93 (2H, t, J=6 Hz, —OCH$_2$—). $\nu_{max}$(film): 2940, 2870, 2790 (CH); 1760, 1740(C=O); 1200, 1170 (—C—O—C) cm$^{-1}$. m/e 271; C$_{16}$H$_{33}$NO$_2$ requires 271.

EXAMPLE 3

Preparation of Decyl (4-methyl-1-piperazinyl)acetate

Following the general procedure of Example 2, a mixture of decyl chloroacetate (5 g, 0.021 mol) and 1-methylpiperazine (2 equivalents) in 20 ml of ether was stirred for one and one-half days. Work-up as in Example 2 gave 6 g of a liquid product (92% yield), which was chromatographed through a column of silica gel using ethyl acetate as the eluent. $^1$HNMR(CCl$_4$) 0.73(3H, t, CH$_3$); 1.13[16H, s, broad, —(CH$_2$)$_8$—]; 2.03 (3H, s, CH$_3$N—); 2.27(8H, multiplets, —NCH$_2$CH$_2$—); 2.91(2H, s, —CH$_2$N—); 3.87(2H, t, J=6 Hz, OCH$_2$) $\nu_{max}$ (film): 2940, 2870, 2800, 2700 (CH); 1755 (C=O); 1170 (—C—O—C)cm$^{-1}$. m/e 298; C$_{17}$H$_{34}$N$_2$O$_2$ requires 298.

EXAMPLE 4

Preparation of Representative Intermediates and Final Products

Alkyl chloroacetates were prepared in almost quantitative yields by reaction of chloromethyl chloroformate with n-alkanols in the presence of triethylamine, as in Example 1. The purification of these compounds is straight-forward, by column chromatography using silica gel as the supporting material and chloroform as the eluent. Yields are summarized in TABLE 1 below.

TABLE 1

$$CH_3-(CH_2)_n-\underset{R_4}{\overset{R_3}{\underset{|}{\overset{|}{C}}}}-O-\overset{O}{\overset{\|}{C}}-\underset{R}{\overset{|}{CH}}-Cl \quad (II)$$

| Name of Compound | R | n | $R_3$ | $R_4$ | Yield (%) |
|---|---|---|---|---|---|
| tetradecyl chloroacetate | H | 12 | H | H | 85 |
| dodecyl chloroacetate | H | 10 | H | H | 94 |
| decyl chloroacetate | H | 8 | H | H | 100 |
| octyl chloroacetate | H | 6 | H | H | 100 |

The penetration enhancers of formula (I) were also prepared in high yield, as in Example 2, by condensation of the alkyl chloroacetates with excess amine. Purification is also simple due to the high yields and high $R_f$ values on thin layer chromatography using ethyl acetate as the developing solvent. Because of their low ultraviolet absorption, the purity of the products was checked by thin layer chromatography, using Analtech HPTLC-GHLF tlc plates, ethyl acetate as the developing system and iodine vapor as the visualizing agent. Nuclear magnetic resonance, infrared and mass spectra were consistent with the assigned structures. Yields are summarized in Table 2 below:

TABLE 2

$$CH_3-(CH_2)_n-\underset{R_4}{\overset{R_3}{\underset{|}{\overset{|}{C}}}}-O-\overset{O}{\overset{\|}{C}}-\underset{R}{\overset{|}{CH}}-NR_1R_2 \quad (I)$$

| Name of Compound | R | n | $-NR_1R_2$ | $R_3$ | $R_4$ | Yield (%) |
|---|---|---|---|---|---|---|
| tetradecyl (N,N-dimethylamino)-acetate | H | 12 | $-N(CH_3)_2$ | H | H | 90 |
| dodecyl (N,N-dimethylamino)-acetate | H | 10 | $-N(CH_3)_2$ | H | H | 100 |
| decyl (N,N-dimethylamino)-acetate | H | 8 | $-N(CH_3)_2$ | H | H | 91 |
| octyl (N,N-dimethylamino)-acetate | H | 6 | $-N(CH_3)_2$ | H | H | 72 |
| dodecyl (N,N-diethylamino)-acetate | H | 10 | $-N(C_2H_5)_2$ | H | H | 95 |
| decyl (4-methyl-1-piperazinyl)-acetate | H | 8 | $-N\underset{\diagdown\_\_\diagup}{\diagup^{\frown}\diagdown}N-CH_3$ | H | H | 96 |

EXAMPLE 5

Preparation of Ointment for Evaluation

Ointments were prepared by mixing 100 mg (1%) indomethacin, 500 mg (5%) penetration enhancer and 9400 mg (94%) petrolatum at 55°-60° C. to give a homogeneous dispersion of indomethacin. In each transport study, 30 mg of ointment containing 300 g of indomethacin was applied.

EXAMPLE 6

Preparation of Patch for Evaluation

Patches were prepared by first dissolving 300 mg indomethacin, 400 mg penetration enhancer, 300 mg polyethylene glycol 400 and 800 mg hydroxypropyl cellulose in 20 ml of ethanol. That viscous solution was spread on a backing layer, which was a film of ethoxycellulose, with 0.9 mm of thickness. After drying at 40° C. for one hour, two layer film patches were obtained. Circles with a diameter of 12 mm were used for the transport studies.

EXAMPLE 7

Preparation and Use of the Black Rat Snake Barrier Membrane to Evaluate Drug Penetration A whole shed snake skin from the molt of adult *Elaphe obsoleta* (black rat snake) was obtained from the Animal Care Unit of the University of Kansas. Only the dorsal side of the shed snake skin was used for in vitro penetration studies. The head and tail sections of the snake skin was removed and the remainder of the skin was cut randomly into sections of approximately 2 inches by 2 inches. Each piece of snake skin was hydrated overnight by first soaking the skin in water (about 5 to 10 minutes) until it could be stretched and then placing it on a plastic pan which held some water. The pan was floated on a water-bath at 32° C. overnight.

For the transport studies using ointments, approximately 30 mg of ointment prepared as described in Example 5 was smeared evenly on an area of the 2"×2" snake skin. The ointment was smeared into an essentially circular area approximately 1.77 cm² and having a diameter of approximately 15 mm. The snake skin was then mounted on top of the receptor cell of a verticle diffusion cell assembly in which a small magnetic bar was inserted and filled with an isotonic buffer. A rubber o-ring was placed on top of the skin followed by the placement of the donor cell. The two cells were clamped together and transferred to a water-bath (32° C.) which had several magnetic stirrers placed underneath to stir the contents of the diffusion cells. Samples from the cells were withdrawn periodically by gravity by inputing fresh isotonic buffer into the cell inlets. The first five drops were discarded and the following four drops were collected for analysis. These nine drops of sample solution were approximately equivalent to about 0.20 ml.

The samples were analyzed for the concentration of indomethacin using a Perkin-Elmer ISS-100 HPLC apparatus with a Perkin-Elmer LC90 UV spectrophotometric detector and a Perkin-Elmer ISS-100 automatic sampler with the detection wavelength set at 260 nm. The peak heights of the chromatograms were recorded on a Perkin-Elmer LCI-100 Laboratory Computing Integrator. A reverse phase column, RP-8 Spheri-5, 4.6×100 mm and a guard column OD-GU, purchased from Brownlee Labs, were used in conjunction with the HPLC system. The flow rate was 1.0 ml/min and the solvent system was a mixture of acetonitrile (50%) and a 0.01M phosphate buffer (pH 3.0) (50%).

The concentration in each sample was interpreted from a standard curve which was obtained by plotting the peak areas obtained from HPL chromatograms versus four different standard solutions of indomethacin. The standard curves were linear over a range of concentrations from 2.5 to 10 g/ml. The receptor cell volume was calibrated by weighing the amount of water in the cell. The first sample needs no concentration correction. However, the concentration in the subsequent samples can be corrected by the following equation:

$$\left(\frac{\text{volume withdrawn}}{\text{volume of the receptor cell}} \times X_i\right) + X_{i+1} + Y_i$$

where $X_i$ is number of microgram of indomethacin in the $i^{th}$ with sample. $Y_i$ is the concentration correction for i-1 sample. The volume withdrawn for each sampling is about 0.20 ml.

For the transport studies using patches, the same procedures were used as described above for the ointments, except that patches were prepared as described in Example 6 and the studies were performed using a new diffusion cell in which receptor medium was recirculated through the spectrophotometer to assay automatically at 265 nm.

Statistical analyses were performed using the Student's t-test.

Table 3 below summarizes the transdermal penetration results for representative enhancers of the invention in the ointment studies.

of the relative enhancements listed in Table 3 are based on the early stage or hours of the penetration studies.

Figure 1:
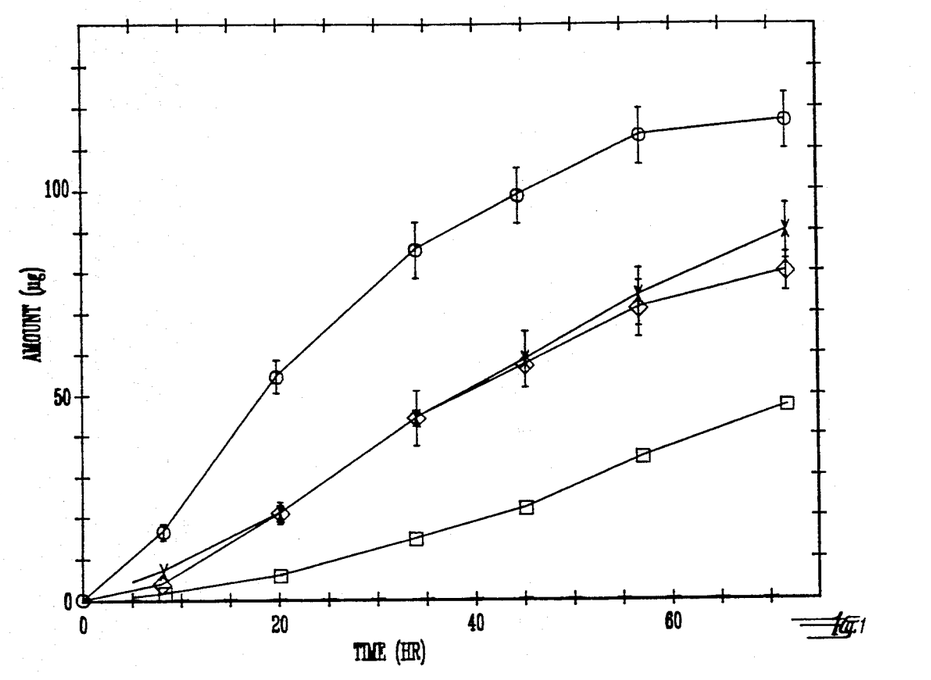
FIG. 1 is a plot of the amount of indomethacin, in μg, detected in the donor cell of a vertical diffusion cell apparatus, versus time, in hours, for an ointment composition containing the prior art enhancer Azone (▲) or one of three representative enhancers of the invention, $CH_3(CH_2)_9OCOCH_2N(CH_3)_2$ (O), $CH_3(CH_2)_{13}OCOCH_2N(CH_3)_2$ (◊) and (□).
Figure 2:
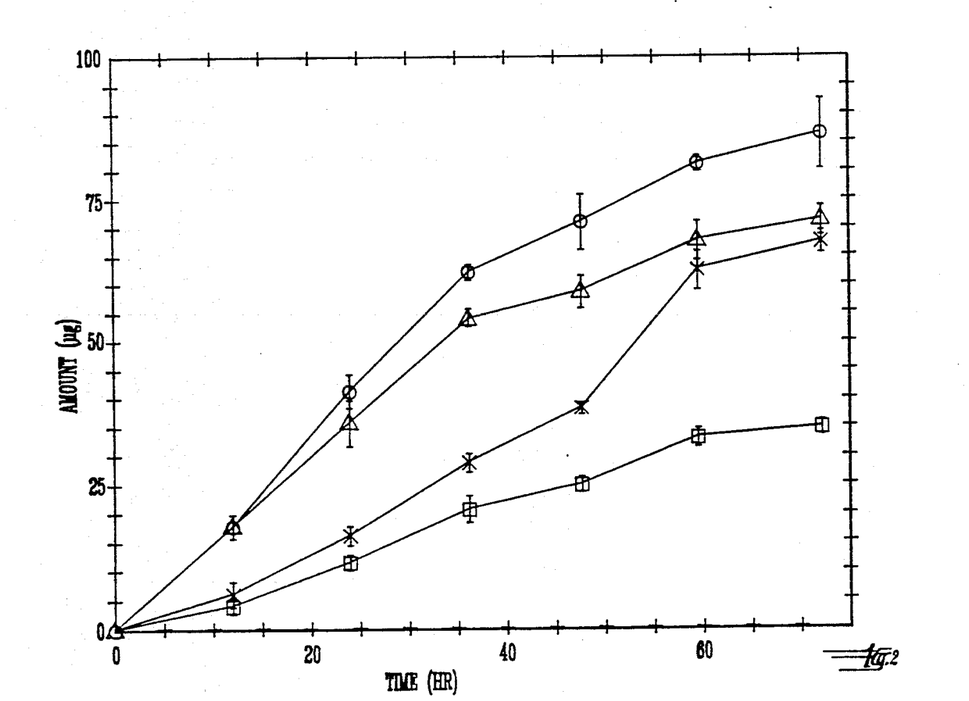
FIG. 2 is a plot as described with reference to FIG. 1 for an ointment composition containing the prior art enhancer Azone (X) or one of three representative enhancers of the invention, $CH_3(CH_2)_7OCOCH_2N(CH_3)_2$ (O), $CH_3(CH_2)_9OCOCH_2N(CH_3)_2$ (▲) and $CH_3(CH_2)_{11}OCOCH_2N(C_2H_5)_2$ (□).
Figure 3:
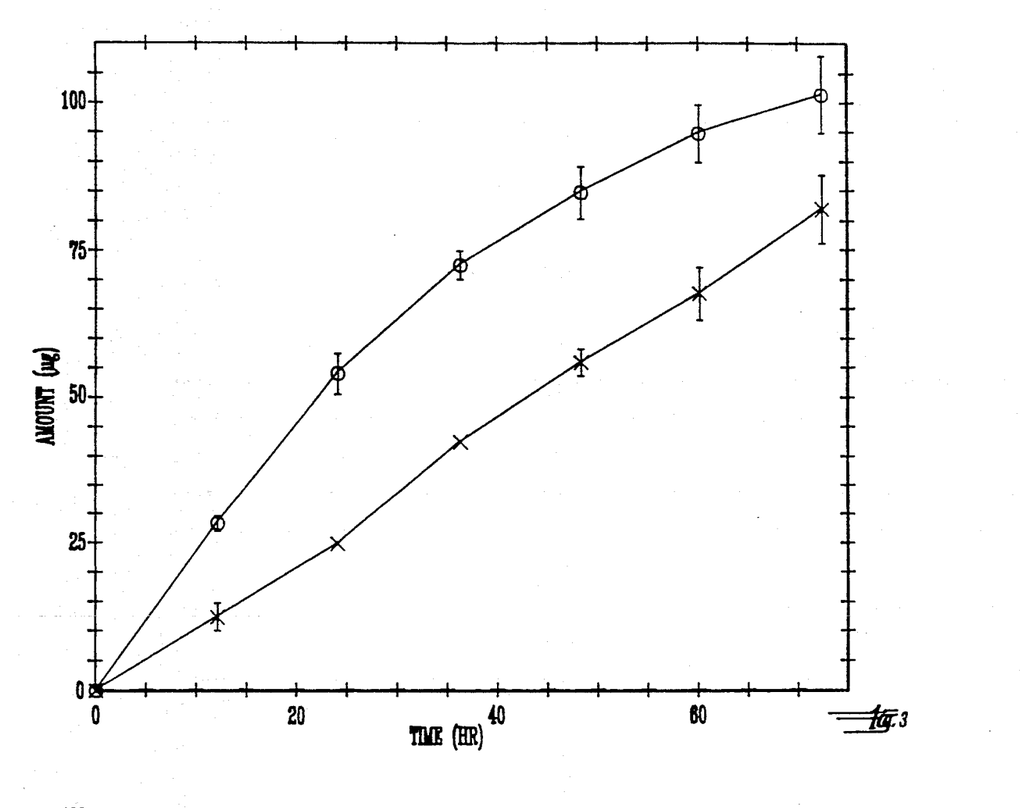
FIG. 3 is a plot as described with reference to FIG. 1 for an ointment composition containing the prior art enhancer Azone (X) or a representative enhancer of the invention, $CH_3(CH_2)_{11}OCOCH_2N(CH_3)_2$ (O).

Results of the ointment studies are shown in FIGS. 1, 2 and 3. At least 3 or 4 diffusion cells were used for each enhancer and mean values for amounts (μg) of indomethacin in the receptor cells are plotted versus time in hours.

In FIG. 1, results are depicted for tests of ointments containing Azone (▲) or one of three enhancers of the invention, namely Compound No. 3 (O), Compound No. 1 (◊) and Compound No. 6 (□). In FIG. 2, results are depicted for tests of ointments containing Azone (X) or one of three enhancers of the invention, namely Compound No. 4 (O), Compound No. 3 (▲) and Compound No. 5 (□). In FIG. 3, results are depicted for tests of ointments containing Azone (X) or a preferred enhancer of the invention, Compound No. 2 (O), also referred to hereinbelow as NDMA.

As can be seen from FIGS. 1 to 3, the new enhancers of the present invention show quick action and exhibit a leveling profile after 24 hours. The fact that the instant enhancers are several times better than Azone at the early time points suggests that the onset of these compounds is short, i.e. they exhibit quick action. This is particularly important in the preparation of topical formulations since one of the most important criteria for enhancers is to have quick action. In receptor cells in

TABLE 3

| Compound No. | Name of Compound | R | n | $-NR_1R_2$ | $R_3$ | $R_4$ | Relative Enhancement % |
|---|---|---|---|---|---|---|---|
| 1 | tetradecyl (N,N-dimethyl-amino)acetate | H | 12 | $-N(CH_3)_2$ | H | H | 100 |
| 2 | dodecyl (N,N-dimethyl-amino)acetate | H | 10 | $-N(CH_3)_2$ | H | H | 200 |
| 3 | decyl (N,N-dimethyl-amino)acetate | H | 8 | $-N(CH_3)_2$ | H | H | 380 |
| 4 | octyl (N,N-dimethyl-amino)acetate | H | 6 | $-N(CH_3)_2$ | H | H | 250 |
| 5 | dodecyl (N,N-diethyl-amino)acetate | H | 10 | $-N(C_2H_5)_2$ | H | H | 70 |
| 6 | decyl (4-methyl-1-piperazinyl)-acetate | H | 8 | $-N\diagup\diagdown N-CH_3$ | H | H | 40 |

Relative penetration enhancements (%) were calculated by $$\frac{\text{Penetration enhancement by the new enhancer}}{\text{Penetration enhancement by Azone}} \times 100\%$$

Azone was selected as the standard for comparison since it is claimed to be an excellent enhancer although it is too toxic; it was assigned a value of 100% enhancement. It has been reported by that the $LD_{50}$ of Azone by intraperitoneal administration is approximately 232 mg/kg.

Penetration that was equal to the penetration of Azone was reported as 100% relative penetration. All which ointments containing enhancers of the present invention were tested, as much as 25 μg of indomethacin were detected in the early stage of less than 12 hours. However, at the same stage, only a few μg of indomethacin were detected in the cells for which Azone was used as the enhancer. The final amounts of indomethacin which penetrated the snake skin in the presence of these enhancers was also high. As high as 117 μg of indomethacin was detected after 72 hours, representing about 40% of the total indomethacin incorporated into the petrolatum ointment.

The effect of Compound No. 2, or NDMA, in ointment on the transport of indomethacin compared with that of Azone is depicted in FIG. 3. The transport of indomethacin accelerated by NDMA was twice that accelerated by Azone during the first 24 hours. The percent of indomethacin across the membrane was $18.2\pm0.9\%$ (n=4, p<0.01 versue Azone) for 24 hours and $34.1\pm2.1\%$ (n=4, p<0.01 versus Azone) for 72 hours when NDMA was present in the ointment, while the values were $8.3\pm0.9\%$ (n=4) for 24 hours and $26.4\pm1.8\%$ (n=4) for 72 hours when Azone was present. The effect of NDMA appeared to be faster than that of Azone. In the absence of either adjuvant, the percent of indomethacin transported was less than 1% for 72 hours (n=4).

Figure 4:
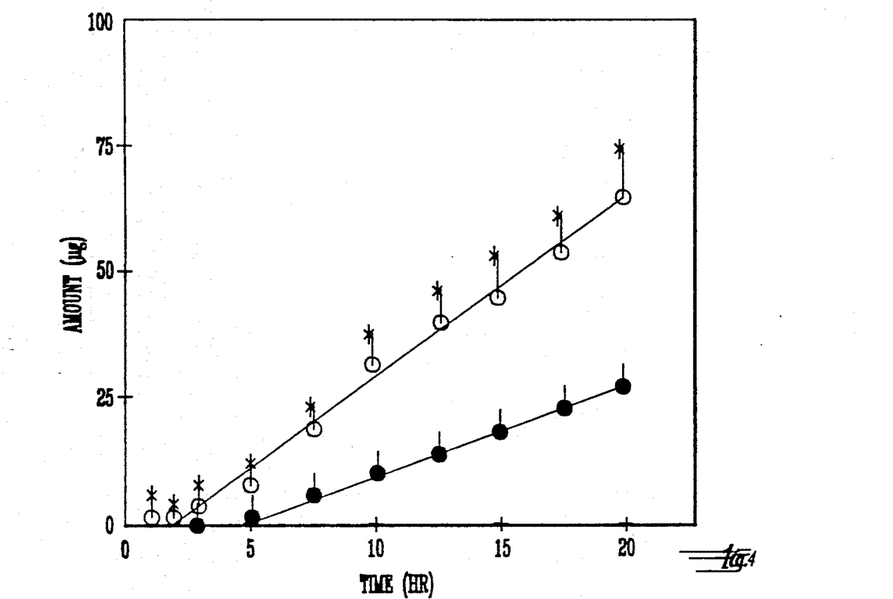
FIG. 4 is a plot as described with reference to FIG. 1 for a patch containing 542±31 mg indomethacin together with a representative enhancer of the invention, $CH_3(CH_2)_{11}OCOCH_2N(CH_3)_2$ (O), and for a patch containing 582±24 mg indomethacin together with dodecyl alcohol (●).

The effect of dodecyl (N,N-dimethylamino)acetate (NDMA) on the transport of indomethacin from a film patch compared to the effect of dodecyl alcohol is shown in FIG. 4. The NDMA (o) patch contained $542\pm31$ mg indomethacin, while the dodecyl alcohol patch contained $582\pm24$ mg indomethacin. The transport of indomethacin enhanced by the presence of NDMA reached steady state flux at about 2 hours, while transport enhanced by dodecyl alcohol reached steady state at about 5 hours. The steady state flux for indomethacin was $3.84\pm0.57$ μg/hour (n=4, p<0.01 versus dodecyl alcohol) in the presence of NDMA, which was 2.5 times greater than that in the presence of dodecyl alcohol ($1.49\pm0.21$ μg/hour, n=4).

EXAMPLE 8

Chronic Toxicity Study

Dodecyl (N,N-dimethylamino)acetate or NDMA (10% w/w) was dispersed in saline (0.85% NaCl in deionized boiled water) with 2% Tween 80. Seven male CF-1 white mice were injected subcutaneously (dorsal site) with the NDMA dispersion at a dose of 1 g/kg daily for seven days. Six control mice were injected with an equivalent volume of 2% Tween 80 saline solution daily for seven days. All mice survived after 14 days.

While the invention has been described in terms of various preferred embodiments, the skilled artisan will appreciate that various modifications, substitutions, omissions and changes may be made without departing the spirit thereof. Accordingly, it is intended that the scope of the present invention be limited solely by the scope of the following claims.

What is claimed is:

1. A pharmaceutical composition for topical administration of a pharmacologically active topical medicament, said composition comprising:
   (a) a pharmacologically active topical medicament in an amount sufficient to achieve a desired pharmacologically effect; and
   (b) a skin penetration enhancer compound of the formula:

wherein n is a whole integer and is 6, 8, 10, or 12, and $R_1$ and $R_2$ are both methyl or both ethyl.

2. A pharmaceutical composition as claimed in claim 1, wherein the penetration enhancing compound of the formula is tetradecyl (N,N-dimethylamino) acetate.

3. A pharmaceutical composition as claimed in claim 1, wherein the penetration enhancing compound of the formula is dodecyl (N,N-dimethylamino) acetate.

4. A pharmaceutical composition as claimed in claim 1, wherein the penetration enhancing compound of the formula is decyl (N,N-dimethylamino) acetate.

5. A pharmaceutical composition as claimed in claim 1, wherein the penetration enhancing compound of the formula is octyl (N,N-dimethylamino) acetate.

6. A pharmaceutical composition as claimed in claim 1, wherein the penetration enhancing compound of the formula is dodecyl (N,N-dimethylamino) acetate.

7. A pharmaceutical composition as claimed in claim 1, said composition being formulated as a cream, lotion, gel, ointment, suppository, spray, aerosol, buccal tablet or sublingual tablet, or as a buccal, gingival, sublingual or palatal patch.

* * * * *